(12) United States Patent
Kang et al.

(10) Patent No.: US 8,496,695 B2
(45) Date of Patent: Jul. 30, 2013

(54) APPARATUS AND METHOD FOR PHOTODYNAMIC DIAGNOSIS AND THERAPY OF SKIN DISEASES AND LIGHT SOURCE SYSTEM THEREOF

(75) Inventors: Uk Kang, Gyeonggi-do (KR); Soo Jin Bae, Gyeonggi-do (KR); Geun Hie Rim, Gyeongsangnam-do (KR); Guang Hoon Kim, Busan (KR); Geri V. Papayan, Saint Petersburg (RU)

(73) Assignee: Korea Electro Technology Research Institute, Changwon, Gyeongsangnam-do (KR)

( * ) Notice: Subject to any disclaimer, the term of this patent is extended or adjusted under 35 U.S.C. 154(b) by 1442 days.

(21) Appl. No.: 11/811,912

(22) Filed: Jun. 11, 2007

(65) Prior Publication Data
US 2008/0147053 A1    Jun. 19, 2008

(30) Foreign Application Priority Data
Dec. 15, 2006    (KR) .................. 10-2006-0128334

(51) Int. Cl.
*A61N 5/06*    (2006.01)
(52) U.S. Cl.
USPC ........................... 607/88; 606/9; 128/898
(58) Field of Classification Search
USPC ..................... 128/898; 606/9; 607/88–94
See application file for complete search history.

(56) References Cited

U.S. PATENT DOCUMENTS

| | | | | | |
|---|---|---|---|---|---|
| 5,363,854 | A | * | 11/1994 | Martens et al. | 600/477 |
| 5,760,407 | A | * | 6/1998 | Margosiak et al. | 250/461.2 |
| 5,851,181 | A | * | 12/1998 | Talmor | 600/407 |
| RE38,670 | E | * | 12/2004 | Asah et al. | 606/9 |
| 7,101,365 | B1 | * | 9/2006 | Sharon | 606/9 |
| 7,282,060 | B2 | * | 10/2007 | DeBenedictis et al. | 607/88 |
| 7,309,335 | B2 | * | 12/2007 | Altshuler et al. | 606/11 |
| 2002/0049432 | A1 | * | 4/2002 | Mukai | 606/9 |
| 2003/0120325 | A1 | * | 6/2003 | Fujisaka et al. | 607/89 |
| 2004/0158300 | A1 | * | 8/2004 | Gardiner | 607/88 |
| 2005/0154382 | A1 | * | 7/2005 | Altshuler et al. | 606/9 |
| 2006/0106435 | A1 | * | 5/2006 | Fraval | 607/88 |
| 2006/0253176 | A1 | * | 11/2006 | Caruso et al. | 607/88 |
| 2007/0049996 | A1 | * | 3/2007 | Black | 607/89 |
| 2010/0145419 | A1 | * | 6/2010 | Fraval | 607/94 |

* cited by examiner

*Primary Examiner* — Henry M Johnson, III
(74) *Attorney, Agent, or Firm* — Edwards Wildman Palmer LLP; Peter F. Corless

(57) ABSTRACT

A system is provided for photodynamic diagnosis and therapy of skin diseases. In particular, a camera head is provided to irradiate a white light, a fluorescent excitation light and a therapeutic light for the photodynamic therapy from the inside of a case onto the skin region being in contact with a view hole. Additionally, a digital color TV camera collects the light from the skin region and outputs a generated image signal. In particular, an image processing and analysis system receives the image signals from the camera head to process, analyze and store the same, displays a color image by the white light, a fluorescent image by the excitation light and the therapeutic light for the photodynamic therapy, obtained by the digital color TV camera, and a synthesized image thereof, and controls the general operations of the camera and the light source system.

29 Claims, 6 Drawing Sheets

APPARATUS AND METHOD FOR PHOTODYNAMIC DIAGNOSIS AND THERAPY OF SKIN DISEASES AND LIGHT SOURCE SYSTEM THEREOF

CROSS-REFERENCE TO RELATED APPLICATION

This application claims under 35 U.S.C. §119(a) the benefit of Korean Patent Application No. 10-2006-0128334 filed on Dec. 15, 2006, the entire contents of which are incorporated herein by reference.

BACKGROUND OF THE INVENTION

1. Field of the Invention

The present invention relates to an apparatus and method for diagnosis and therapy of skin diseases and, more particularly, to an apparatus and method for photodynamic diagnosis and therapy of skin diseases and a light source system thereof that can improve the efficiency of skin diagnosis by accurately analyzing skin conditions using fluorescence and white light simultaneously and further carry out fluorescent diagnosis and photodynamic therapy in the same skin region simultaneously.

2. Background Art

Recently, a variety of skin diagnosis apparatuses can be found in cosmetic shops, skin care clinics, and the like. With the skin diagnosis apparatus, a user can analyze and diagnose its skin condition so as to select cosmetics suitable for the skin condition or to find a problem in its skin condition and obtain a solution to the problem.

Among them, a skin diagnosis apparatus using a diagnostic lamp has been widely used for diagnosing the skin condition by irradiating a light beam of a predetermined wavelength onto the skin and analyzing a specific fluorescence emitted from the skin.

Conventional skin diagnosis apparatuses will be described with reference to literatures as follows.

Skin pores of a human body have sebaceous glands producing sebum.

The sebaceous glands in a healthy body secrete an appropriate amount of sebum from the skin pores to the skin surface to form a sebaceous membrane acting as a natural protecting layer.

However, an unhealthy body secretes an excessive amount of sebum and the sebum excessively secreted soon becomes oxidized by air.

Then, the oxidized sebum becomes stickier and clogs the pores.

Bacteria propagate in the thus clogged pores and porphyrins are produced from the bacteria.

The produced porphyrin emits light in response to ultraviolet light.

Accordingly, a skin diagnosis apparatus using porphyrin properties responsive to ultraviolet light has been developed.

The conventional skin diagnosis apparatus uses a method in which an ultraviolet lamp irradiates a patient's entire face in a dark box to observe a change in fluorescence intensities with naked eyes through a detector.

Meanwhile, optical fiber light sources based on the use of various kinds of lamp, such as halogen, xenon, metal-halide, mercury, etc., which are well known for the purpose of photodynamic diagnosis and therapy of diseases are developed and widely used.

Such lamps have been selected to meet the apparatus requirements in terms of specific medical purposes and means, technical and economical aspects.

In a case where a complicated operation that should use a wide range of light intensities or a variety of light beams of selective wavelengths is required, the use of a single lamp could not provide an optimal method in general.

In this case, the developer of the apparatus has depended on a lamp having a specific function or used a plurality of lamps simultaneously to overcome the drawbacks.

Especially, it has been known that it is necessary to observe geometry, position, color of an examination region by a white light in addition to the observation of fluorescence generated from the examination region by an excitation light irradiation in diagnosing diseases using fluorescence.

Advantages, possibilities and recent trends in use of fluorescence diagnosis (FD) and photodynamic therapy (PDT) of skin diseases using a photosensitizer including 5-aminolevulinic acid (5-ALA) have been described in the reference literature (C. Fritch and T. Ruzichka, "Fluorescence Diagnosis and Photodynamic Therapy of Skin Diseases", Atlas and Handbook, 2003, Springer-Verlag. Wien).

According to the literature, a fluorescence image of a dermal layer is recorded in the form of a photograph in such a manner that the examination region is exposed to ultraviolet light of a Wood's lamp in a dark room for 0.25 to 1.5 seconds to take a photograph and the photograph is developed with a high speed film such as 1600 ASA.

Meanwhile, U.S. Pat. No. 5,363,854 has disclosed a method for detecting anomalies of the skin, more particularly melanoma, and an apparatus for carrying out the method, in which an ordinary video camera fixed with a light source in a picture processing unit is used for detecting a fluorescence picture of an examination region and a reference picture.

The apparatus includes a light source for illuminating a two-dimensionally extending examination region of the skin, successively, with ultraviolet light range and with visible light.

The camera records a fluorescence picture of the examination region having signal values $F(x,y)$ at its picture points x,y in response to the illumination with ultraviolet light and a reference picture having signal values $R(x,y)$ at its picture points x,y in response to the illumination with visible light.

A memory stores the signal values of at least one of the fluorescence picture and said reference picture, and a processor responsive to the memory produces an output picture having respective signal values $A(x,y)$ at its picture points x,y which are formed from respective quotients $F(x,y)/R(x,y)$ of the signal values of the fluorescence and reference pictures at the same picture points.

The image observed through an ocular of the apparatus is reorganized with two color images through a dichroic mirror.

The light source operates under continuous conditions or under impulse conditions and it saves energy and reduces the effect of extraneous light under the impulse conditions.

The apparatus for detecting skin diseases includes an excitation light source for generating fluorescence from the examination region.

The fluorescence generated along the reference light are divided by a beam splitter and sent to respective optical paths, the respective optical paths produce images in the examination region, and an optical coupler provides the images produced by the respective optical paths so that a user can observe the images with naked eyes.

U.S. Pat. No. 5,760,407 has proposed a device for the identification of acne, microcomedones, and bacteria on human skin.

Meanwhile, for the purpose of the diagnosis of skin diseases, there have been developed a series of photo-diagnostic methods using spectroscopy and imaging methods.

For the purpose of the skin therapy, there have been disclosed phototherapy methods by the action of electromagnetic radiation, and fluorescence diagnosis and photodynamic therapy (PDT) occupy an important place in such a series of photo-diagnostic methods.

In case of the fluorescence diagnosis, fluorescent characteristics observed in the diseased tissue region and in the normal tissue region are different from each other, and this difference is shown as emitted wavelength and fluorescence intensity.

One of the drawbacks in the spectroscopic wavelength calibration is that the spatial resolution in the examination region is low and the number of spots examined is small.

The method of obtaining the fluorescence image from the examination region eliminates the above drawback and the fluorescence images observed in most cases are given in the form of a monochrome fluorescence image.

Accordingly, for the purpose of an accurate morphological analysis, a color image acquired simultaneously by a white light from the same examination region is supplemented with the monochrome fluorescence image [simultaneous acquisition and display of morphological (color image) and physiological (fluorescence image) information] (DYADERM professional, Biocam GmbH; http://www.biocam.de].

However, as the monochrome fluorescence image loses information showing the difference of wavelengths in the individual skin regions, the quality of the image is substantially poor and it makes it difficult to investigate the cause of the fluorescence in study on the intrinsic fluorescence characteristics produced in the skin itself.

Meanwhile, it is possible to combine the advantages of the fluorescence spectroscopy method and the fluorescence imaging method by a multispectral imaging system [Hewett et al., 2000, "Fluorescence detection of superficial skin cancer," J. Mod. Opt. 47, 2021-2027].

Moreover, the basic spectroscopic information of the fluorescence produced from the skin can be obtained from the visible light region and thereby it is possible to apply a high sensitive color camera to the multispectral imaging system, thus simplifying the configuration of the apparatus and improving the spatial resolution as well.

A facial image of color fluorescence can be taken using the Clarity Pro facial image scanner manufactured by Moritex USA Inc. [http://www.moritexusa.com] and this scanner provides a fluorescence image using an ultraviolet light illumination and mainly concentrates on the examination of the facial skin.

However, UV-Scope of Moritex USA Inc. can examine other regions of the body as well as the face. The configuration of such an apparatus has been disclosed in European Patent No. EP1488737, Chinese Patent No. CN1572250 and U.S. Patent Publication No. 2004-0257439 A1, and shown in FIG. 1 of the present application.

According to the skin observing apparatus capable of observing the skin tissue, it is possible to observe blotches caused from subcutaneous pigmentation and skin roughness caused from keratin abrasion by a single unit of an image pick-up device without using polarization.

The apparatus includes an image pick-up head 3 having a view hole 2 to be in contact with a skin, provided inside the image pick-up device, an image pick-up device 4 for picking-up an image of the skin through the view hole 2, and an illumination system comprising three systems 5A, 5B and 5C.

That is, the illumination system comprises a tissue observing illumination system 5A for irradiating a white light to the view hole 2 along an image pick-up light axis X, a keratin abrasion observing illumination system 5B for irradiating a white light to the view hole 2 from the lateral direction thereof, and a subcutaneous pigment observing illumination system 5C for irradiating a UV-light to the view hole 2.

However, the above apparatus has some drawbacks in that it may be harmful to the skin since it observes the fluorescence (UV imaging mode) only by the UV excitation means and it may reduce the possibility of the fluorescence diagnosis since the depth of the skin diagnosis is low.

Moreover, it is efficient that a blue light having a main peak at a wavelength of 400 nm be used rather than the ultraviolet light for the purpose of the diagnosis of acne disease, skin cancer, etc., since the photosensitizers (photo-accelerators or contrast agents) including 5-ALA and the porphyrins in Propionibacterium acnes have a main absorption band in the vicinity of a wavelength of 400 nm.

The above apparatus has a further drawback in that it cannot carry out the photodynamic therapy (PDT).

In addition, the apparatus has a drawback in that, if the UV LED lights are arranged circularly around the image pick-up light axis X and the illumination light axes $X_C$ are collected to the center of the view hole 2, the illuminated regions by the LED lights should overlap each other based on the light axis X in order to obtain a UV illumination light of a uniform intensity in the view hole 2, and thereby the illuminated regions by the LED lights are limited to a very narrow range.

A specific light source is used for the purpose of the photodynamic therapy. The light source for the photodynamic therapy used in the skin care field may be coherent or non-incoherent. The non-coherent light source is generally cheaper than the coherent one and can be used together with other photosensitizers as it allows the illumination in a wider wavelength range.

One of the non-coherent light sources widely used for carrying out the photodynamic therapy is Model LC-122M manufactured by LumaCare [http://www.lumacare.com/gen-prod.htm; Non-Coherent Light Sources for PDT].

As the light source in such a light source system, a halogen lamp having a wavelength range of 400 nm to 800 nm and an output power of 20 mW/cm$^2$ to 1000 mW/cm$^2$ is mainly used and the light is transmitted through replaceable optical guides to the necessary region of the patient's skin.

However, the above apparatus has no function of taking a fluorescence image like the other non-coherent light sources having optical fibers for carrying out the PDT.

As described above, the apparatus for providing the fluorescence image and the apparatus for the photodynamic therapy using the non-coherent light source having light guides for the light transmission are separately manufactured in accordance with the intended use.

That is, such apparatuses are manufactured separately for the fluorescence diagnosis and not for the photodynamic therapy or, on the contrary, for the photodynamic therapy and not for the fluorescence diagnosis.

SUMMARY OF THE INVENTION

The present invention has been made in an effort to solve the above problems, and an object of the present invention is to provide an apparatus and method for photodynamic diagnosis and therapy of skin diseases and a light source system thereof that can improve the efficiency of skin diagnosis by accurately analyzing skin conditions using fluorescence and white light simultaneously.

Another object of the present invention is to provide an apparatus and method for photodynamic diagnosis and therapy of skin diseases and a light source system thereof that can carry out fluorescent diagnosis and photodynamic therapy in the same skin region simultaneously.

In a preferred embodiment, the present invention provides a system for photodynamic diagnosis and therapy of skin diseases comprising: a camera head including a case having a view hole, provided in front thereof, to be in contact with a skin region, a white light source provided so as to irradiate a white light from the inside of the case through the view hole onto the skin region, a digital color TV camera provided in the rear of the case, the camera head being provided to irradiate the white light, a fluorescence excitation light and a therapeutic light for the photodynamic therapy from the inside of the case onto the skin region being in contact with the view hole, and the digital color TV camera collecting the light from the skin region and outputting a generated image signal; a light source system, connected to the case of the camera head through a light guide capable of light transmission, for providing the fluorescence excitation light, the therapeutic light for the photodynamic therapy and the white light to be irradiated onto the skin region to the camera head; and an image processing and analysis system for receiving the image signal from the camera head to process, analyze and store to same, for displaying a color image by the white light, a fluorescence image by the excitation light and the therapeutic light for the photodynamic therapy, obtained by the digital color TV camera, and a synthesized image thereof, and for controlling the general operations of the camera head and the light source system.

In another aspect, the present invention provides a method for photodynamic diagnosis and therapy of skin diseases comprising: bringing a skin region into contact with a view hole formed in a front surface of a case in a camera head; illuminating the skin region, brought into contact with the view hole, with a white light using a white light source in the case; obtaining a color image signal based on a reflected light from the illumination of the white light using a digital color TV camera provided in the rear of the case, and processing and storing the color image signal transmitted from the digital color TV camera using an image processing and analysis system; illuminating the skin region, brought into contact with the view hole, with an excitation light supplied from a light source system to the inside of the case through a light guide; obtaining a fluorescence image signal based on the fluorescence by the illumination of the excitation light using the digital color TV camera, and processing and storing the fluorescence image signal transmitted from the digital color TV camera using the image processing and analysis system; and displaying a color image and a fluorescence image obtained by the image processing and analysis system, or a synthesized image thereof, and analyzing the images.

In a further aspect, the present invention provides a light source system for photodynamic diagnosis and therapy of skin diseases, the light source system comprising: a case, through which light is finally output, including a light output unit connected to an end portion of a light guide; a plurality of light sources operated in the case by receiving electric power from a power unit; a switching path-coupling unit, provided in the case, for selectively transmitting wavelengths of lights emitted from the plural light sources; a filter exchange unit, provided between the switching path-coupling unit and the light output unit in the case, including a plurality of optical filters for selectively transmitting wavelengths of light; through the switching path-coupling and a control unit, communicably connected to the image processing and analysis system through a remote control interface, for controlling the operations of the power unit, the switching path-coupling unit and the filter exchange unit in accordance with signals transmitted from the image processing and analysis system, and controlling the general operations of the light source system.

DETAILED DESCRIPTION OF THE INVENTION

Figure 1:
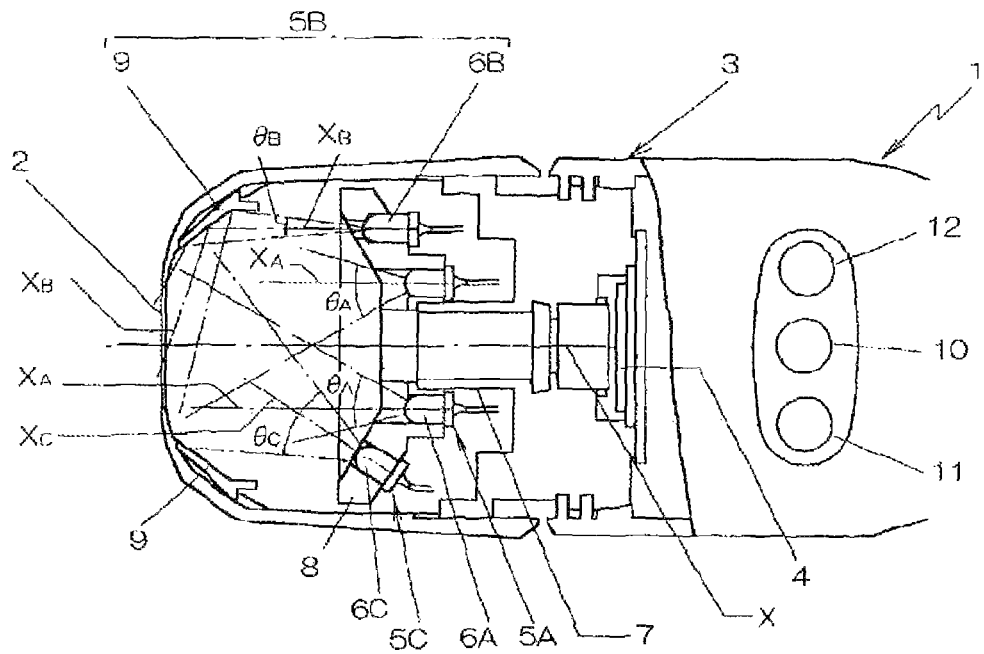
FIG. 1 is a configuration diagram showing a conventional skin observing apparatus.

Reference will now be made in detail to the preferred embodiment of the present invention, examples of which are illustrated in the drawings attached hereinafter, wherein like reference numerals refer to like elements throughout. The embodiments are described below so as to explain the present invention by referring to the figures.

The present invention provides an apparatus and method for diagnosis and therapy of skin diseases. More particularly, the present invention provides an apparatus and method for photodynamic diagnosis and therapy of skin diseases and a light source system thereof that can improve the efficiency of skin diagnosis by accurately analyzing skin conditions using fluorescence and white light simultaneously and further carry out fluorescent diagnosis and photodynamic therapy in the same skin region simultaneously.

Figure 2:
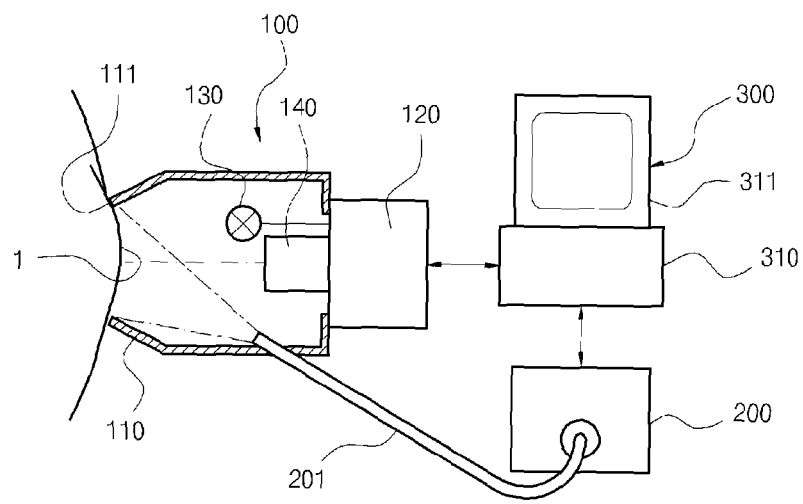
FIG. 2 is a configuration diagram showing an apparatus for photodynamic diagnosis and therapy in accordance with the present invention.
Figure 3:
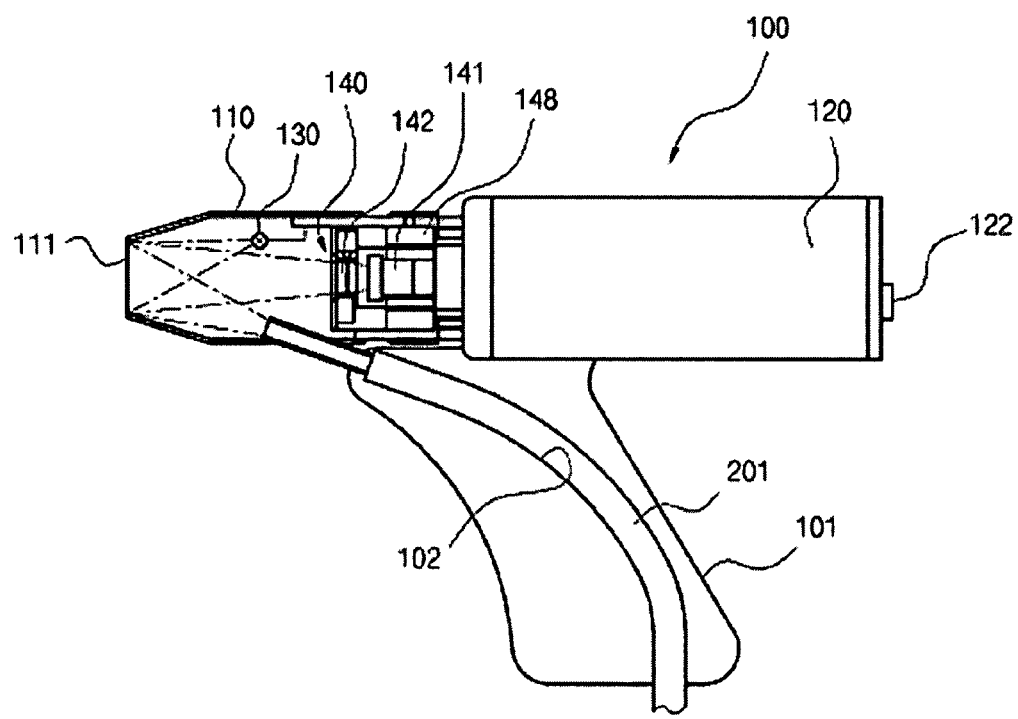
FIG. 3 is a cross-sectional view showing a detailed configuration of a camera head for the skin diagnosis and therapy in the apparatus for photodynamic diagnosis and therapy in accordance with the present invention.

FIG. 2 is a configuration diagram showing an apparatus for photodynamic diagnosis and therapy in accordance with the present invention, and FIG. 3 is a cross-sectional view showing a detailed configuration of a camera head for the skin diagnosis and therapy in the apparatus for photodynamic diagnosis and therapy in accordance with the present invention.

The apparatus for photodynamic diagnosis and therapy in accordance with the present invention includes a camera head 100 for taking an image by irradiating light to a skin region 1 for the diagnosis and therapy and collecting the light from the skin region 1 and, at the same time, for providing the taken image to an external image processing and analysis system 300.

In a preferred embodiment shown in FIG. 3, the camera head 100 is adapted to be held by a hand and to be in contact with the skin region 1 for the diagnosis and therapy. For this purpose, the camera head 100 includes a handle 101, a case 110 with internal components, and a digital color TV camera 120 equipped with a CCD chip.

In such a configuration, the case 110 and the digital color TV camera 120 are mounted fixedly on the top of the handle 101, in which the digital color TV camera 120 is mounted in the rear thereof and the case 100 with internal components are mounted in front of the digital color TV camera 120.

The case 110 of the camera head 100 is manufactured using a light impermeable material and includes a view hole 111 formed in the front portion thereof to be in contact with the skin region 1 for the diagnosis and therapy so as to observe the skin region 1. Through the view hole 111, the light is irradiated to the skin region 1 and collected to take an image.

That is, the camera head 100 is used in a manner that the view hole 111 of the case 110 is in contact with the skin region 1 so as to set a focus on the front surface thereof and to level the skin surface. At this time, the case 110 prevents the entrance of external light noise into the camera head 100.

Moreover, a light guide 201 connected from an external light source system 200 is formed in the case 110 of the camera head 100. The light guide 201 comprises an optical fiber guide or a liquid light guide capable of light transmission. In order to irradiate the light supplied from the light source system 200 through the light guide 201 onto the skin region 1 through the view hole 111 on the front surface of the case 110, an end portion of the light guide 201 is fixed inserted into the case 110 such that the light irradiation direction is toward the view hole 111.

Since an output angle of the light supplied from the light guide 201 is more than 70° which is very larger than that of an LED and the light output power is greater than that of the LED, it is easy to ensure the uniformity of the light illumination and the light output power for the photodynamic therapy in the view hole 111.

In order to obtain a more uniform illumination, an optical system may be arranged between the end portion of the light guide 201 and the view hole 111.

For example, the optical system may include an optical adapter comprising a plurality of lenses capable of providing a uniform light output power and formed in the end portion of the light guide 201 or a diffusion plate for uniformly diffusing the light incident to the view hole 111.

Moreover, the end portion of the light guide 201 fixed inserted into the case 110, through which the light is emitted from the light guide 201, may be configured in the form of a bundle comprising a plurality of light guides capable of illuminating the skin region at various angles.

Accordingly, the light supplied from the light source system 200 is applied to the camera head 100 through the light guide 201, and the light emitted from the end portion of the light guide 201 in the case 110 of the camera head 100 illuminates the selected skin region 1 through the view hole 111 in the front surface of the case 110.

As shown in FIG. 2, the light guide 201 is inserted into an internal passage 102 of the handle 101 and connected to the inside of the case 110 of the camera head 100 through the internal passage 102.

The light source system 200 for providing the light used for the fluorescence excitation and the photodynamic therapy supplies a fluorescence excitation light irradiated onto the skin region 1 through the light guide 201 and is mainly composed of a plurality of lamps and a plurality of optical filters as will be described in detail below.

The light source system 200 may be configured to emit light in the wavelength range of 400 nm to 750 nm.

Meanwhile, the optical system 140 mounted in front of the digital color TV camera 120 in the case 110 of the camera head 100 is an element for forming an image of the skin region 1 on a TV sensor 121 surface of the digital color TV camera 120 in a given wavelength range, in which the wavelength transmission of the light reaching the optical system 140 is determined by the filters inserted into the optical system 140.

A white light source 130 of small size manufactured for recording an ordinary TV images may be arranged inside the case 110 of the camera head 100. If the white light source 130 emits a white light, the white light is projected onto the skin region 1 through the view hole 111 on the front surface of the case 110.

The white light source 130 provided inside the case 110 of the camera head 110 is used to illuminate the skin region 1 in order for the digital color TV camera 120 to take an image and becomes a light source used to examine the skin surface.

The digital color TV camera 120 mounted in the top rear portion of the handle 101 of the camera head 100 includes an RGB matrix. The TV camera 120 obtains a color image of the skin region 1 based on the reflected light of the white light and a fluorescence image of the skin region 1 based on the fluorescence of the excitation light supplied from the light source system 200 to be described in detail below.

A connector 122 is provided in the rear end portion of the digital color TV camera 120, and a high-speed digital interface 231 thereof is connected to an image processing and analysis system 300 through a signal transmission cable 123. That is, the digital color TV camera 120 of the camera head 100 is coupled to the image processing and analysis system 300 through the cable 123 so as to transmit the image signal taken. Accordingly, the image signal output from the digital color TV camera 120 is transmitted through the cable 123 to the image processing and analysis system 300.

The image processing and analysis system 300 may comprise a computer 310, i.e., a control means, to which the digital color TV camera 120 is connected through the cable 123, and a monitor 311 attached thereto.

In the image processing and analysis system 300, the computer 310 processes, analyzes and stores the image signal transmitted from the digital color TV camera 120, and the monitor 311 displays the color image by the white light and the fluorescence image by the fluorescence excitation light and therapeutic light for the photodynamic therapy, obtained by the digital color TV camera 120, or a synthesized image thereof.

Moreover, the image processing and analysis system 300 controls the general operations of the camera head 100 and the light source system 200 in accordance with the operational conditions.

Hereinafter, the optical system will be described in more detail.

As shown in FIG. 3, the optical system 140 broadly includes an object lens 141 for receiving the light reflected from the skin region 1 and a filter exchange unit 142 having a plurality of filters. Moreover, the optical system 140 may include a focus adjustment unit 148 for adjusting the focus of the object lens 141 and a dynamic focus system, i.e., a zoom system, (not depicted) for the zoom operation of the object lens 141.

Figure 4:
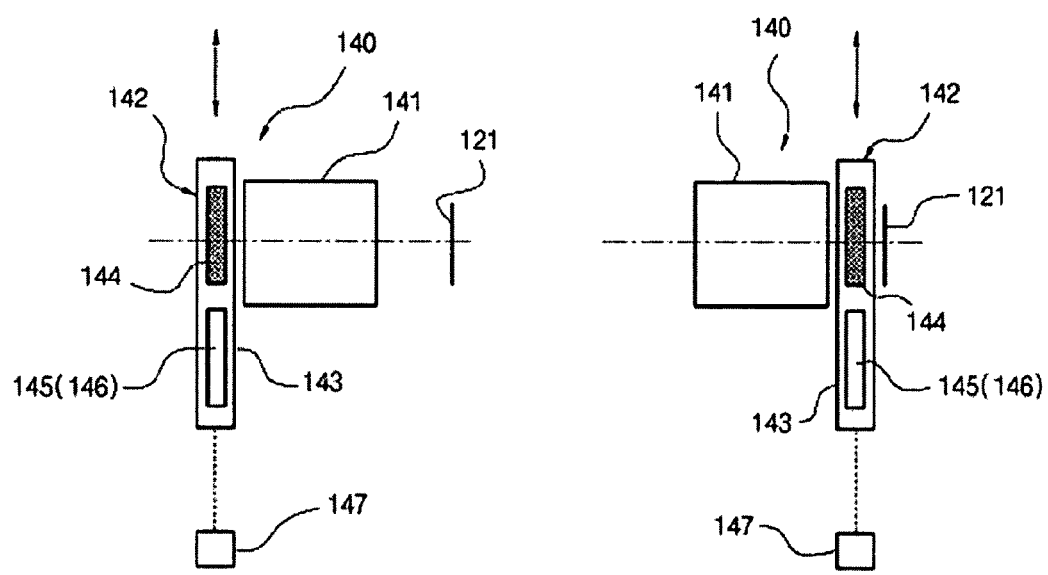
FIG. 4 illustrates example diagrams of an object lens and a filter exchange unit in an optical system in accordance with the present invention.

FIG. 4 illustrates two configuration examples of the object lens 141 and the filter exchange unit 142 in the optical system 140.

The positions of the object lens 141 and the filter exchange unit 142 may be designed in two ways as shown in the left and right drawings in FIG. 4. That is, as shown in the left drawing in FIG. 4, the object lens 141 may be positioned in front of the TV sensor 121 and the filter exchange unit 142 may be positioned in front of the object lens 141. Moreover, as shown in the right drawing in FIG. 4, the filter exchange unit 142 may be positioned in front of the TV sensor 121 and the object lens 131 may be positioned in front of the filter exchange unit 142.

That is, it is possible to place the filter exchange unit 142 between the skin surface and the object lens 141 or between the object lens 141 and the TV sensor 121 of the digital color TV camera 120.

Accordingly, if the object lens 141 receives the light reflected from the skin region 1 and transmits the same to the TV sensor 121, the digital color TV camera 120 converts the reflected light into an image signal, i.e., an electronic signal showing an image, and transmits the same to the computer 310 of the image processing and analysis system 300.

The filter exchange unit 142 comprises a plurality of optical filters including a long pass barrier emission filter 144 for shielding the excitation light or the therapeutic light under fluorescence-excitation light conditions, a color conversion filter 145 for reproducing the skin color itself and improving the color under white light observation conditions, and an IR cut-off filter 146 for cutting off unnecessary infrared rays.

Here, the long pass barrier emission filter 144 is mounted to prevent the entrance of the excitation light or the therapeutic light into the camera, the IR cut-off filter 146 is provided to correct the spectrum characteristics of the white light by cutting off unnecessary infrared rays, thus improving the image quality.

The long pass barrier emission filter 144 is inserted in front of the camera, i.e., on the light path, under fluorescence measurement conditions, i.e., under fluorescence image obtaining conditions. Whereas, the IR cut-off filter 146 is established on the light path under white light observation conditions, i.e., under color image obtaining conditions.

In brief, the long pass barrier emission filter 144 prevents the entrance of the excitation light emitted in the case 110 into the TV sensor 121 while the TV camera 120 obtains a fluorescence image of the skin region 1 based on the fluorescence of the excitation light, and the IR cut-off filter 146 prevents the entrance of the IR rays into the TV sensor 121 while the TV camera 120 obtains a color image of the skin region 1 based on the reflected light of the white light.

In the filter exchange unit 142 configured as described above, the optical filters may be mounted replaceably in holders included in respective positions of a filter mounting frame 143. The filter mounting frame 143 is positioned in front of the object lens 141 or in the rear of the object lens 141, i.e., in front of the camera, and mounted movably in the horizontal direction by a manual or automatic position adjuster 147 for filter exchange, e.g., a linear actuator.

Accordingly, an optical filter to be used is positioned in front of the camera 120 with the movement of the filter mounting frame 143, thus enabling the selection of filters.

Figure 5:
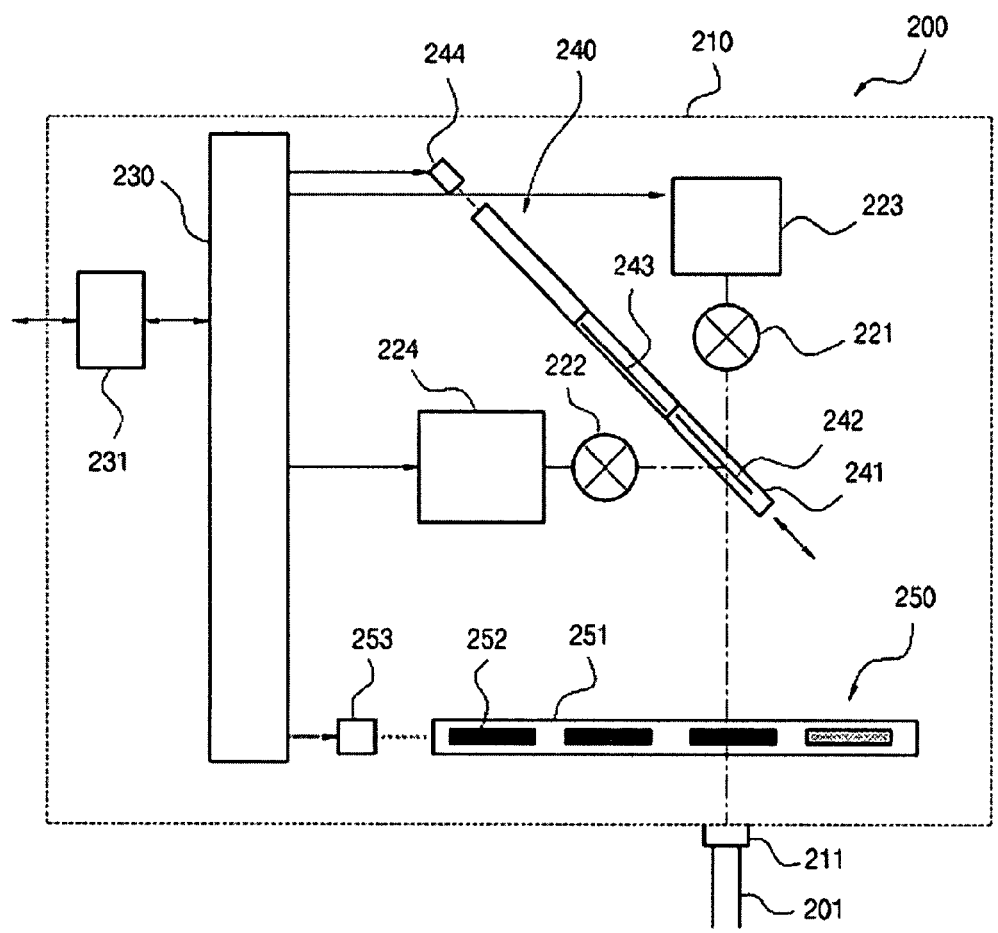
FIG. 5 is a configuration diagram showing a light source system applicable to the apparatus for photodynamic diagnosis and therapy in a preferred embodiment of the present invention.
Figure 6:
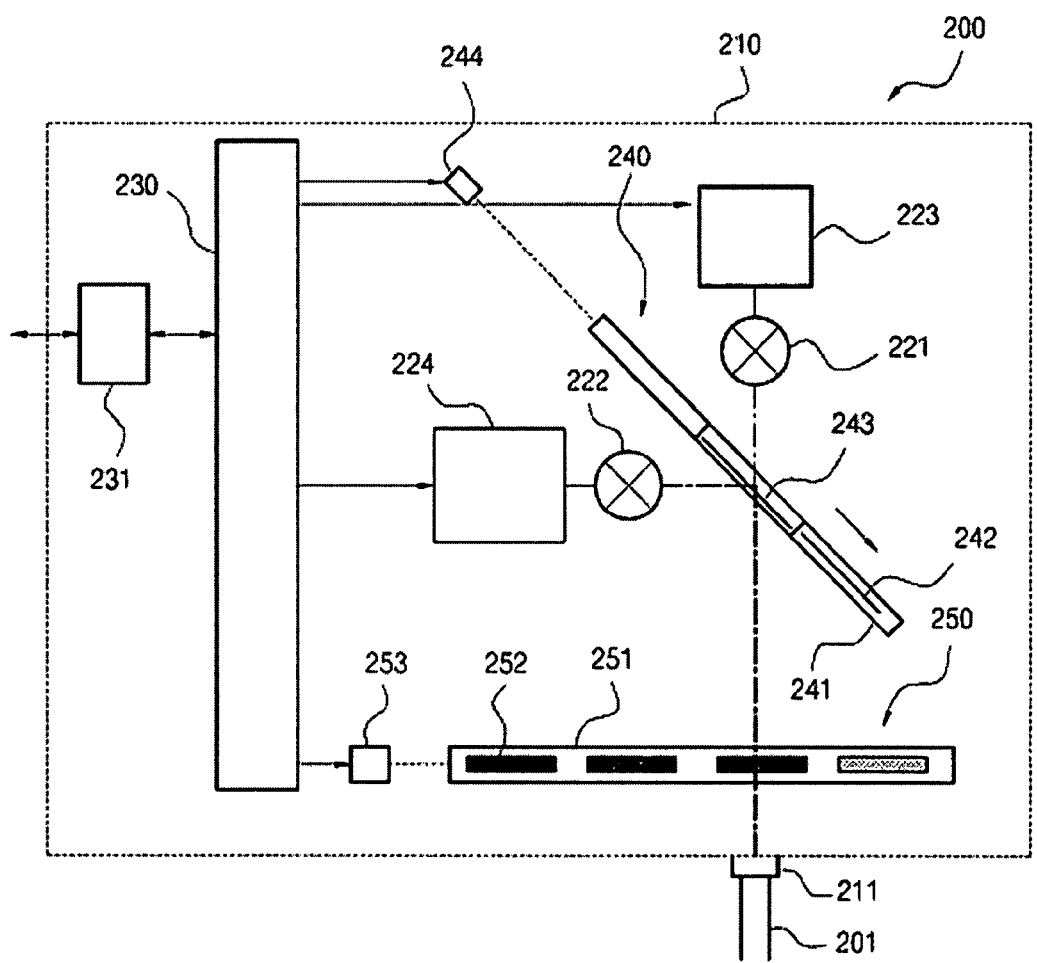
FIGS. 6 and 7 are state diagrams showing different light selections in the light source system in accordance with the present invention.
Figure 7:
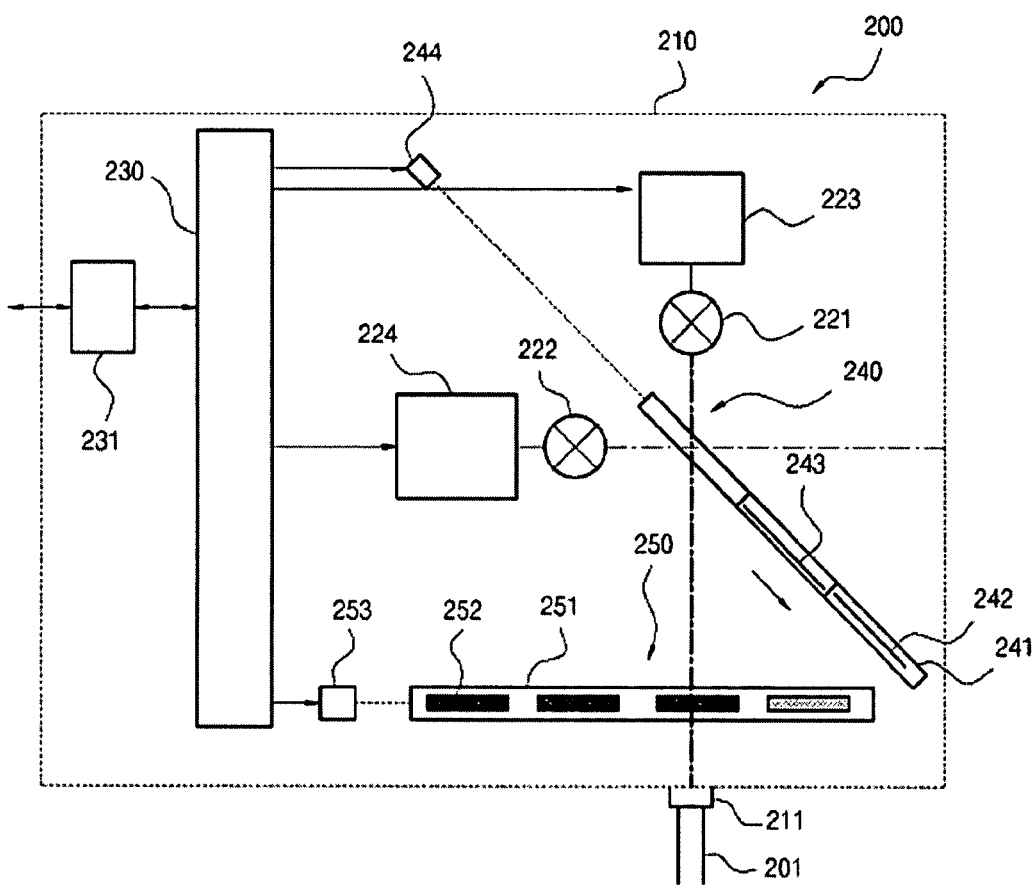

Next, FIG. 5 is a configuration diagram showing a light source system applicable to the apparatus for photodynamic diagnosis and therapy in a preferred embodiment of the present invention, and FIGS. 6 and 7 are state diagrams showing different light selections in the light source system in accordance with the present invention. With reference to the figures, a preferred embodiment of the light source system available will be described as follows.

An excitation light source is required to examine the difference in intensities of autofluorescence light in a skin tissue according to whether there exists an abnormality in the skin tissue or the difference in intensities of secondary fluorescence light between in the abnormal region and in the normal region when injecting a contrast agent, and an excitation light source or a therapeutic light source for the photodynamic therapy is required. The light source system 200 is an element for providing the excitation light and therapeutic light.

Besides, the light source system 200 may provide a white light.

As depicted in the figures, the light source system 200 in accordance with the present invention, provided in the form of a complex light source, comprises a case 210, light sources 221 and 222, power units 223 and 224, a control unit 230, a remote control interface 231, a switching path-coupling unit 240, and a filter exchange unit 250 including a plurality of filters.

First, an end portion of the light guide 201 is connected to a light output unit 211 of the case 210, and the light output unit 211 is a portion through which the light produced for the fluorescence diagnosis and photodynamic therapy is finally output and is connected to the light guide 201 for providing light to the camera head 100.

Accordingly, the light output through the light output unit 211 is supplied along the light guide 201 to the camera head 100 and finally irradiated onto the skin region 1 brought into contact with the front surface of the case 110 of the camera head 100.

Moreover, two kinds of light sources, i.e., two different lamps 221 and 222, operated by receiving electric power from the power units 223 and 224, are provided in the case 210. Furthermore, the control unit 230 controlling the operations of the power units 223 and 224 and the respective units 240 and 250 and controlling the general operations of the light source system 200 is established in the case 210.

The control unit 230 communicably connected to the computer 310 of the image processing and analysis system 300 through the remote control interface 231 controls the operations of the respective units 223, 224, 240 and 250 in accordance with signals transmitted from the image processing and analysis system 300 and outputs control signals for controlling the general operation of the light source system 200.

The two lamps 221 and 222 provided as light sources are lighted when receiving electric power from the respective power units 223 and 224 to emit light and they may be arranged so as to emit light on both sides of the switching path-coupling unit 240 in 90° direction.

In the preferred embodiment of the present invention, a mercury short arc lamp may be used as one of the two lamps (hereinafter referred to as a first lamp 221) and a tungsten halogen lamp may be used as the other of the two lamps (hereinafter referred to as a second lamp 222).

Next, in the light source system 200, the lights emitted from the two lamps 221 and 222 pass through the switching path-coupling unit 240 and the filter exchange unit 250 in turn and then are introduced into the light output unit 211. A dichroic mirror 242 and an opaque mirror 243 are mounted in two holders of three holders in the frame 241 of the switching path-coupling unit 240, and no mirror is mounted in the rest holder to be an empty holder, as shown in FIG. 5.

Here, the dichroic mirror 242 used has a high light transmissivity in the short wavelength range below 500 nm.

The frame 241 of the switching path-coupling unit 240 is arranged in an inclined direction, for example 40°, between the two lamps 221 and 222 movably in the inclined direction by a position adjuster 244 driven under the control of the control unit 230.

Accordingly, with the movement of the frame 241 of the switching path-coupling unit 240, it is possible to selectively transmit the lights of the two lamps or the light of one of the two lamps.

The filter exchange unit 250 is disposed between the switching path-coupling unit 240 and the light output unit 211 and a plurality of optical filters 252 is mounted in a filter mounting frame 251 of the filter exchange unit 250.

Moreover, the filter exchange unit 250 may comprise a filter for fluorescence excitation, a filter for photodynamic therapy, a filter for white light observation, and the like. In more detail, the filter exchange unit 250 may comprise a short-wave-pass filter, a long-wave-pass filter, a narrow-band-pass filter, a broad-band-pass filter, a multi-band-pass filter, and the like.

The optical filters 252 may be replaceably mounted in the holders included in the respective positions of the frame 251 of the filter exchange unit 250. The frame 251 is positioned in front of the switching path-coupling unit 240 movably in the horizontal direction by an ordinary position adjuster 253 for filter exchange, e.g., a linear actuator.

Accordingly, an optical filter to be used is positioned in front of the switching path-coupling unit 240 with the movement of the filter mounting frame 251, thus enabling the selection of filters.

Moreover, as described above in detail, the operations of the switching path-coupling unit 240 and the filter exchange unit 250 are controlled by the control unit 230, and the position adjusters 244 and 253 of the respective units 240 and 250 are controlled by control signals output from the control unit 230, thus enabling the selection of lights and the selection of filters.

Hereinafter, the respective operational states of the light source system will be described with reference to FIGS. 5 to 7.

FIG. 5 shows a state of the switching path-coupling unit 240 in which the dichroic mirror 242 is selected, the dichroic mirror 242 being positioned on the path of the lights emitted from the respective lamps 221 and 222.

The light spectrum characteristics of the dichroic mirror 242 in the switching path-coupling unit 240 are selected in the following manner.

In the wavelength range having a high light transmissivity, the light intensity of the first lamp 221 is greater than that of the second lamp 222, whereas, in the wavelength range having a high reflectivity, the light intensity of the second lamp 222 is greater than that of the first lamp 221.

In such a case, the lamps 221 and 222 provide high intensities in a wide wavelength range due to the difference in light intensities according to the respective wavelengths of the lamps in the selected dichroic spectrum.

That is, if the light intensity of the first lamp 221 is large in the short wavelength range, if that of the second lamp 222 is large in the long wavelength range, and if the spectrum characteristics of the dichroic mirror 242 exhibit a high light transmissivity in the short wavelength range and a high light reflectivity in the long wavelength range, the lights emitted from the first and second lamps 221 and 222 have high intensities in a wide wavelength range by passing through the dichroic mirror 242 to the light output unit 211 as shown in FIG. 5.

FIG. 6 shows a state of the switching path-coupling unit 240 in which the opaque mirror 243 is selected, the opaque mirror 243 being positioned on the path of the lights emitted from the respective lamps 221 and 222.

As shown in the figure, if only the second lamp 222 is used, the light of the first lamp 221 is cut off by the opaque mirror 243 and only the light of the second lamp 222 is reflected by the opaque mirror 243 (downwardly in the figure) to pass through the optical fiber 252 and then output through the light output unit 211 to the light guide 201.

Moreover, FIG. 7 shows a state of the switching path-coupling unit 240 in which the empty holder is selected, the empty holder being positioned on the path of the lights emitted from the respective lamps 221 and 222.

As shown in the figure, if only the first lamp 221 is used, the light of the first lamp 221 passes through the empty holder and the optical filter 252 without energy loss and then is output though the light output unit 211 to the light guide 201.

Next, the configuration of the preferred embodiment in accordance with the present invention will be illustrated and described in detail with reference to the accompanying drawings; however, the present invention is not limited thereto.

First, the camera head 100 is brought into contact with the skin region 1. More particularly, the view hole 111 of the front surface of the case 110 is brought into contact with the tissue surface of the skin region 1 to be diagnosed and treated, and the light emitted through the light guide 201 from the light source system 200 is irradiated onto the skin region 1.

As the light guide 201, a liquid light guide with a diameter of 8 mm (Series 380, Lumatec GmbH, Deisenhofen, Germany) may be used.

Then, the object lens 141 (focus F=16 mm, aperture number f/2) projects the skin region 1 having a filed of view of 12×16 mm onto the sensor surface of the digital color TV camera 120.

The object lens 141 may be provided such that the focus adjustment is made by the focus adjustment unit 148 and provide detail focuses on various surfaces of the skin region by means of the focus adjustment unit 148.

Moreover, the filter exchange unit 142 having optical filters is positioned in front of the object lens 141, in which the long pass barrier emission filter (GG-475, Schott AG) is used to prevent the entrance of the excitation light into the TV camera 120 under fluorescence measurement conditions, and the IR cut-off filter is used to correct the spectrum characteristics of the white light by cutting off unnecessary infrared rays under white light observation conditions, thus improving the quality of the image taken by the TV camera 120.

The two optical filters are selectively used in accordance with the use conditions.

The TV camera 120 may be one formed with the progressive scan RGB CCD-array CXD3611Ar chip (SONY) with 567×768 pixels, and the frame speed of the camera is 25 Hz.

The TV camera 120 is connected to the computer 310 of the image processing and analysis system 300 through a high-speed digital interface IEEE-1394 in the connector 122, and data, control signals and power voltages are transmitted through the interface IEEE-1394 (the digital interface is operated by the computer and IEEE-1394 protocol).

Meanwhile, the light source system 200 provided in the form of a complex light source supplies light to be irradiated onto the skin region 1 through the light guide 201. In the preferred embodiment of the present invention, the mercury short arc lamp is provided as the first lamp 221 and the tungsten halogen lamp is used as the second lamp 222.

The mercury short arc lamp emits light with a high intensity in the short wavelength range (up to 500 nm) and the tungsten halogen lamp emits light with a high intensity in the long wavelength range (more than 500 nm).

Accordingly, when the two lamps 221 and 222 are simultaneously lighted and the dichroic mirror 242 showing a high transmissivity and reflexivity in the vicinity of 500 nm is positioned on the light path, it is possible to provide a higher intensity in a wide wavelength range by the dichroic mirror 242.

At this time, the wavelength range to be applied may be 400 nm to 750 nm in consideration of the light transmissivities of the optical parts including the light guide.

With the use of the light source system 200, it is possible to carry out the fluorescence diagnosis and photodynamic therapy on the skin region simultaneously. During the photodynamic therapy, the light is supplied with an output density above 100 mW/cm$^2$ in the interested spectrum range.

The light source system 200 is provided to operate in three conditions such as a fluorescence mode F, a white light mode W, and a photodynamic therapeutic mode P. For this purpose, the optical filters 252 combined in accordance with the respective modes are provided in the filter exchange unit 250, in which several optical filters 252 can be used in the F and P modes simultaneously.

For example, in case of the filters for the fluorescence excitation transmitted in the blue-violet region (400 nm to 450 nm), the absorption wavelength bands of numerous photosensitizers coincide with the spectrum of the region where the filters are arranged.

Accordingly, the above optical filters can be simultaneously used for the fluorescence diagnosis and photodynamic therapy.

Like this, the digital color TV camera 120 mounted in the handle 101 of the camera head 100 obtains a color image based on the reflected light of the white light irradiated onto the skin region 1 from the white light source 130 in the camera head 100 or the light source system 200. Moreover, the digital color TV camera 120 obtains a fluorescence image based on the fluorescence of the excitation light or the therapeutic light for the photodynamic therapy irradiated from the light source system 200 through the light guide 201 and the camera head 100 to the skin region 1. Furthermore, the control means, i.e., the computer 310 of the image processing and analysis system 300 receives the color image by the white light and the fluorescence image by the excitation light obtained by the digital color TV camera 120 to process, analyze, store and synthesize the same. In addition, the display means, i.e., the monitor 311 displays the color image by the thus obtained white light, the fluorescence image or the synthesized image thereof.

According to the apparatus for photodynamic diagnosis and therapy of the present invention configured as described above, it is possible to illuminate the skin region with the white light so as to obtain and record an ordinary image from the skin region, and to illuminate the skin region with the excitation light and therapeutic light so as to obtain and record a fluorescence image.

Moreover, it is possible to analyze the thus obtained images by means of the computer 310 and to irradiate the therapeutic light onto the skin region for the photodynamic therapy.

Furthermore, the ordinary image and the fluorescence image are obtained in the color (RGB) frame, and especially the fluorescence image is an image obtained from an autofluorescence light in a tissue according to whether there exists an abnormality in the skin tissue, or from a secondary fluorescence result after injecting a photosensitizer (or contrast agent) into the body.

The ordinary image and the fluorescence image obtained by the TV camera 120 in the apparatus of the present invention are overlapped (synthesized) with each other in a given frame that can change the brightnesses of the respective images and displayed in the form of a frame through the display means of the image processing and analysis system 300, i.e., the monitor 311 connected to the computer 310. Here, the brightnesses of the respective images can be adjusted manually or through the computer 310.

Moreover, in the measurement of the reflected light of the white light and the fluorescence of the excitation light, it is possible to carry out image correction using a standard image stored in advance, and the color image by the white light and the fluorescence image by the excitation light obtained in the analysis of the ordinary image and the fluorescence image can be used to evaluate the brightness, color and morphological parameter of the analysis object, i.e., the skin region.

For example, an orange-red fluorescence is observed in the diseased skin region, in which Propionibacterium acnes proliferate. Accordingly, the orange-red fluorescence can be used for the analysis for the photodynamic therapy of Propionibacterium acnes.

Moreover, the light source system irradiates light in the wavelength range of 400 nm to 750 nm, i.e., in the absorption range of the photo-sensitizer with an output density of more than 100 mW/cm$^2$, and the photo-sensitizer may be produced internally or injected from the outside.

Furthermore, the excitation light in the violet-blue spectrum range (400 nm to 450 nm) is illuminated onto the diseased skin region to obtain a fluorescence image and further used for the photodynamic therapy of the diseased skin region.

In addition, in the process of the light irradiation for the photodynamic therapy, the first fluorescence intensity is measured and recorded in a given light wavelength range, and the light irradiation for the photodynamic therapy is stopped after photobleaching the fluorescence from the first fluorescence intensity value to a designated range.

As described above, according to the apparatus and method for photodynamic diagnosis and therapy of skin diseases and the light source system thereof in accordance with the present invention, it is possible to improve the efficiency of skin diagnosis by accurately analyzing the skin conditions using the color image by the white light and the fluorescence image by the excitation light simultaneously and to carry out the fluorescent diagnosis and photodynamic therapy in the same region of the skin simultaneously.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A system for photodynamic diagnosis and therapy of skin diseases comprising:
    a camera head including a case having a view hole, provided in front thereof, to be in contact with a skin region, a light guide provided in the rear of the case, the camera head being provided to irradiate a white light, a fluorescence excitation light and a therapeutic light for the photodynamic therapy from the inside of the case onto the skin region being in contact with the view hole, and a digital color TV camera collecting the light from the skin region and outputting a generated image signal;
    a light source system, connected to the case of the camera head through the light guide capable of light transmission, providing the fluorescence excitation light, the therapeutic light for the photodynamic therapy and the white light simultaneously to be irradiated onto the skin region to the camera head; and
    an image processing and analysis system for receiving the image signal from the camera head to process, analyze and store to same, for displaying a color image by the white light, a fluorescence image by the excitation light and the therapeutic light for the photodynamic therapy, obtained by the digital color TV camera, and a synthesized image thereof, and for controlling the general operations of the camera head and the light source system,
    wherein the light source system includes a plurality of light sources and a switching path-coupling unit having an empty holder with no mirror and two holders with a dichroic mirror and an opaque mirror respectively for selectively transmitting wavelengths of light emitted from the plurality of light sources.

2. The system of claim 1, wherein the camera head comprises a handle, in which the case and the digital color TV camera are fixedly provided on the top thereof, adapted to be held by a hand.

3. The system of claim 2, wherein the handle further comprises an internal passage and the light guide is inserted and connected to the case through the internal passage.

4. The system of claim 1, wherein the light guide comprises an optical fiber light guide.

5. The system of claim 1, wherein the light guide comprises a liquid light guide.

6. The system of claim 1, wherein an end portion of the light guide is inserted and connected to the case such that the light irradiation direction is toward the view hole, and the light guide is provided in the form of a bundle comprising a plurality of light guides capable of illuminating the skin region at various angles.

7. The system of claim 1, wherein the camera head comprises an optical system, provided in front of the digital color TV camera in the case, for forming an image of the skin region on a TV sensor of the digital color TV camera in a given wavelength range, the optical system comprising a filter exchange unit including a plurality of optical filters for selectively transmitting wavelengths of light reached from the skin region, and an object lens for receiving the light reflected from the skin region.

8. The system of claim 7, wherein the filter exchange unit comprises a long pass barrier emission filter for shielding the excitation light under fluorescence conditions.

9. The system of claim 7 or 8, wherein the filter exchange unit comprises an infrared cut-off filter for cutting off infrared rays under white light observation conditions.

10. The system of any one of claims 7 and 8, wherein the filter exchange unit comprises a color conversion filter for reproducing the skin color itself and improving the color under white light observation conditions.

11. The system of claim 7, wherein the optical system further comprises a focus adjustment unit for adjusting the focus of the object lens.

12. The system of claim 7, wherein the optical system further comprises a dynamic focus system, i.e., a zoom system, for the zoom operation of the object lens.

13. The system of claim 1, wherein the digital color TV camera is connected to a computer of the image processing and analysis system through a high-speed digital interface thereof.

14. The system of claim 13, wherein the digital interface is operated by the computer and IEEE-1394 protocol.

15. The system of claim 1, wherein the main spectrum range of the light emitted from the light source system is 400 nm to 750 nm.

16. The system of claim 1 or 15, wherein the light source system comprises: a case, through which light is finally output, including a light output unit connected to the end portion of the light guide; a plurality of light sources operated in the case by receiving electric power from a power unit; a switching path-coupling unit, provided in the case, for selectively transmitting wavelengths of lights emitted from the plural light sources; a filter exchange unit, provided between the switching path-coupling unit and the light output unit in the case, including a plurality of optical filters for selectively transmitting wavelengths of light; and a control unit, communicably connected to the image processing and analysis system through a remote control interface, for controlling the operations of the power unit, the switching path-coupling unit and the filter exchange unit in accordance with signals transmitted from the image processing and analysis system, and controlling the general operations of the light source system.

17. The system of claim 16, wherein a first lamp and a second lamp are provided as light sources in the case so as to emit light on both sides of the switching path-coupling unit 240 in 90° direction.

18. The system of claim 17, wherein the switching path-coupling unit comprises a frame arranged in an inclined direction between the first and second lamps movably in the inclined direction by a position adjuster driven under the control of the control unit, wherein a dichroic mirror and an opaque mirror are mounted in two holders of three holders in the frame, respectively, and the rest holder remains as an empty holder so as to selectively transmit the lights of the two lamps or the light of one of the two lamps.

19. The system of claim 18, wherein the dichroic mirror has a high light transmissivity in the short wavelength range below 500 nm.

20. The system of claim 17 or 18, wherein the first lamp is a mercury short arc lamp and the second lamp is a tungsten halogen lamp.

21. The system of claim 16, wherein the filter exchange unit comprises a short-wavepass filter, a long-wave-pass filter, a narrow-band-pass filter, a broad-band-pass filter, and a multi-band-pass filter, respectively selected in accordance with fluorescence excitation, photodynamic therapy, and white light observation.

22. A method for photodynamic diagnosis and therapy of skin diseases comprising:
   bringing a skin region into contact with a view hole formed in a front surface of a case in a camera head;
   illuminating the skin region, brought into contact with the view hole, with a white light using a light guide in the case;
   obtaining a color image signal based on a reflected light from the illumination of the white light using a digital color TV camera provided in the rear of the case, and processing and storing the color image signal transmitted from the digital color TV camera using an image processing and analysis system;
   illuminating the skin region, brought into contact with the view hole, with an excitation light supplied from a light source system to the inside of the case through the light guide simultaneously with the white light;
   obtaining a fluorescence image signal based on fluorescence by the illumination of the excitation light using the digital color TV camera, and processing and storing the fluorescence image signal transmitted from the digital color TV camera using the image processing and analysis system; and
   displaying a color image and a fluorescence image obtained by the image processing and analysis system, or a synthesized image thereof, and analyzing the images,
   wherein the light source system includes a plurality of light sources and a switching path-coupling unit having an empty holder with no mirror and two holders with a dichroic mirror and an opaque mirror respectively for selectively transmitting wavelengths of light emitted from the plurality of light sources.

23. The method of claim 22 further comprising irradiating a therapeutic light supplied from the light source system to the case through the light guide onto the skin region, brought into contact with the view hole, thus carrying out photodynamic therapy.

24. The method of claim 23, wherein the therapeutic light irradiation for photodynamic therapy comprises recording a measured value of a first fluorescence intensity within a given light wavelength range, and stopping the light irradiation for photodynamic therapy after photobleaching the fluorescence from the first fluorescence intensity value to a designated range.

25. The method of any one of claims 22 to 24, wherein the therapeutic light is irradiated from the light source system through the light guide in the wavelength range of 400 nm to 750 nm and with an output density above 100 mW/cm$^2$.

26. The method of claim 22, wherein the fluorescence image is obtained from an autofluorescence light result in a skin tissue according to whether there exists an abnormality in the skin tissue.

27. The method of claim 22, wherein the fluorescence image is obtained from a secondary fluorescence result after injecting a contrast agent into a body.

28. The method of claim 22, wherein the analysis of the color image and the fluorescence image obtained by the image processing and analysis system carries out evaluation of brightness, color and morphological parameter of the skin region.

29. The method of claim 22 further comprising carrying out image correction including brightness using a standard image obtained and stored in advance from a standard object having the same or similar optical characteristics as those of an examination object against the color image and the fluorescence image obtained from the skin region of the examination object.

* * * * *